US012632961B2

(12) United States Patent
Huang et al.

(10) Patent No.: US 12,632,961 B2
(45) Date of Patent: May 19, 2026

(54) AUTOMATIC CALCULATION METHOD OF GRAY-TO-WHITE-MATTER RATIO FOR HEAD COMPUTED TOMOGRAPHY OF PATIENTS WITH CARDIAC ARREST

(71) Applicants:NATIONAL TAIWAN UNIVERSITY, Taipei City (TW); NATIONAL TAIWAN UNIVERSITY HOSPITAL, Taipei City (TW)

(72) Inventors: Chien-Hua Huang, Taipei City (TW); Chien-Yu Chi, Taipei City (TW); Liang-Wei Wang, Taipei City (TW); Yu-Jen Su, Taipei City (TW); Weichung Wang, Taipei City (TW); Hsin-Han Tsai, Taipei City (TW); Cheyu Hsu, Taipei City (TW)

(73) Assignees: NATIONAL TAIWAN UNIVERSITY, Taipei City (TW); NATIONAL TAIWAN UNIVERSITY HOSPITAL, Taipei City (TW)

( * ) Notice: Subject to any disclaimer, the term of this patent is extended or adjusted under 35 U.S.C. 154(b) by 290 days.

(21) Appl. No.: 18/393,588

(22) Filed: Dec. 21, 2023

(65) Prior Publication Data

US 2024/0212139 A1 Jun. 27, 2024

Related U.S. Application Data

(60) Provisional application No. 63/434,483, filed on Dec. 22, 2022.

(51) Int. Cl.
G06T 7/11 (2017.01)
G06T 5/40 (2006.01)
(Continued)

(52) U.S. Cl.
CPC .............. G06T 7/0012 (2013.01); G06T 5/40 (2013.01); G06T 7/11 (2017.01); G16H 30/40 (2018.01);
(Continued)

(58) Field of Classification Search
CPC ........... G06T 7/0012; G06T 7/11; G06T 5/40; G06T 2207/10081; G06T 2207/10088;
(Continued)

(56) References Cited

U.S. PATENT DOCUMENTS

2021/0264623 A1* 8/2021 Tandon ..................... G06T 7/38
2024/0104705 A1* 3/2024 Zhao ......................... G06T 7/11

FOREIGN PATENT DOCUMENTS

CN 115482183 A * 12/2022 ............... G06N 3/02

OTHER PUBLICATIONS

Nurhayati et al, Filter Selection and Feature Extraction to Distinguish Types of CT Scan Images, 2021, 4th International Seminar on Research of Information Technology and Intelligent Systems, pp. 1-7. (Year: 2021).*

(Continued)

*Primary Examiner* — Kathleen M Broughton
(74) *Attorney, Agent, or Firm* — RABIN & BERDO, P.C.

(57) ABSTRACT

An automatic calculation method of gray-to-white-matter ratio for head computed tomography of patients with cardiac arrest is disclosed and includes an image registration step, a K-means segmentation step, a segmentation refinement step and a GWR calculation step. Measure the gray-white-matter ratio through brain computed tomography early after cardiac arrest to automatically identify the corpus callosum, caudate nucleus, putamen, and posterior branch of the internal brain cyst. It is a 3D three-dimensional structure rather than a manually selected flat circular area to evaluate the effectiveness of predicting neurological prognosis at discharge.

9 Claims, 8 Drawing Sheets

(51) Int. Cl.
*G06T 7/00* (2017.01)
*G16H 30/40* (2018.01)
*G16H 50/30* (2018.01)

(52) U.S. Cl.
CPC ........................ *G16H 50/30* (2018.01); *G06T 2207/10081* (2013.01); *G06T 2207/10088* (2013.01); *G06T 2207/30016* (2013.01)

(58) Field of Classification Search
CPC .......... G06T 2207/30016; G16H 30/40; G16H 50/30
See application file for complete search history.

(56) References Cited

OTHER PUBLICATIONS

Pociask et al, Fully Automated Lumen Segmentation Method for Intracoronary Optical Coherence Tomography, 2018, J. Healthcare Engineering, 2018, pp. 1-13. (Year: 2018).*

Zhou et al, A fusion algorithm based on composite decomposition for PET and MRI medical images, 2022, Biomedical Signal Processing and Control 76 (2022) pp. 1-15. (Year: 2022).*

Goyal et al, Development of a Stand-Alone Independent Graphical User Interface for Neurological Disease Prediction with Automated Extraction and Segmentation of Gray and White Matter in Brain MRI Images, 2019, J. Healthcare Engineering, (2019) pp. 1-21. (Year: 2019).*

Goyal et al, Development of a Stand-Alone Independent Graphical User Interface for Neurological Disease Prediction with Automated Extraction and Segmentation of Gray and White Matter in Brain MRI Images (Year: 2019).*

* cited by examiner

CC (Genu)

CN

PU

PIC

CN

PU

PIC

CC (Splenium)

CC (Splenium)

AUTOMATIC CALCULATION METHOD OF GRAY-TO-WHITE-MATTER RATIO FOR HEAD COMPUTED TOMOGRAPHY OF PATIENTS WITH CARDIAC ARREST

CROSS-REFERENCE TO RELATED APPLICATIONS

This application claims the priority of US provisional application U.S. 63/434,483, filed on Dec. 22, 2022, which is incorporated herewith by reference.

PRIOR ART

After struggling to rescue, the Out-of-Hospital Cardiac Arrest (OHCA) patient suffered from mild to severe hypoxic-ischemic brain injury, resulting in various neurological defects, including coma, which caused serious consequences to family members and doctors. Follow-up medical and financial burden. Hypoxic brain injury results in cerebral edema, reduced cortical gray matter attenuation, or loss of normal gray-white differentiation. Early prediction of neurological outcome is important in cardiac arrest patients. In clinical practice, several neurological status measurement methods have been proposed after resuscitation and return of spontaneous circulation (ROSC), including neurological examination, brain non-contrast computed tomography, somatosensory evoked potential (SSEP), serum biomarkers, electroencephalography (EEG) and diffusion-weighted magnetic resonance imaging (DW-MRI). Recent guidelines recommend only non-contrast computed tomography of the brain as an early prognostic tool and to be evaluated within 24 hours of ROSC. Gray-white-matter ratio (GWR) is the most important clue to early hypoxic brain lesions after cardiac arrest. However, emergency or critical care physicians are unable to quantitatively measure gray-to-white matter ratio in point-of-care imaging systems.

The gray-to-white-matter ratio obtained from brain computed tomography (CT) is an important factor in early prediction of patient prognosis. Currently, the manual calculation method is used. Please refer to FIG. 1, the manual calculation method is that the doctor divides the corpus callosum (CC), caudate nucleus (CN), and putamen (PU) of the left and right brains on specific slices and the posterior limb of the internal capsule (PIC) are marked with a circular area of approximately 10 mm², as shown in FIG. 1. Then the gray-to-white-matter ratio formula is applied to obtain the gray-to-white-matter ratio of the patient. The formula is GWR=(CN+PU)/(CC+PIC).

However, the above manual calculation method requires doctors to manually annotate some specific locations, which is impractical in emergency situations.

BACKGROUND OF THE INVENTION

The present invention relates to a technology for predicting cardiac arrest, in particular to an automatic calculation method of gray-to-white-matter ratio for head computed tomography of patients with cardiac arrest.

SUMMARY OF THE INVENTION

A primary objective of the present invention is to provide an automatic calculation method of gray-to-white-matter ratio for head computed tomography of patients with cardiac arrest. The gray-to-white-matter ratio is measured through brain computed tomography early after cardiac arrest to automatically identify the corpus callosum, caudate nucleus, putamen, and posterior branch of the internal brain capsule. It is a 3D three-dimensional structure rather than a manually circled flat circular area to evaluate the effectiveness of predicting neurological prognosis at discharge.

An automatic calculation method of gray-to-white-matter ratio for head computed tomography of patients with cardiac arrest is disclosed. The method comprises an image registration step: performing an alignment on a patient's head computed tomography image and a standard brain MRI image; an image segmentation step: applying the patient's head computed tomography image to an transformation of the alignment to obtain an aligned patient's computed tomography image, then removing a skull to obtain a brain image, and then using a K-Means segmentation to obtain a gray matter mask and a white matter mask of a whole brain; a segmentation refinement step: filtering the gray matter mask and the white matter mask separately, using a morphology to perform a noise removal process, then filtering again, and merging the gray matter mask and the white matter mask to obtain a refined standard brain annotation; and a gray-to-white-matter ratio calculation step: converting the refined standard brain annotation from a standard brain domain back to a patient computed tomography domain by an inverse transformation to obtain a brain mask, and finally, applying a formula based on the patient's head computed tomography image to calculate a gray-to-white matter ratio.

In some embodiments, the image registration step further comprises performing a pre-process on the patient's head computed tomography image.

In some embodiments, the pre-process is contrast limited adaptive histogram equalization.

In some embodiments, the alignment is applied a known standard brain annotation to the patient's head computed tomography image.

In some embodiments, the transformation in the image segmentation step is a vector field that combines affine transformation and nonlinear transformation, and the inverse transformation is the inverse transformation of this vector field.

In some embodiments, in the segmentation refinement step, using the parts of gray matter and white matter in the known standard brain annotation to filter the gray matter mask and the white matter mask, and using the known standard brain annotation to perform the step of filtering again.

In some embodiments, in the segmentation refinement step, using a close operator and an open operator in the morphology to perform the noise removal process.

In some embodiments, the noise removal process includes filling small holes and removing speckle noise.

In some embodiments, in the gray-to-white-matter ratio calculation step, the brain mask includes a corpus callosum mask, a caudate nucleus mask, a putamen mask, and a posterior limb of the internal capsule mask for the left and right brains.

In some embodiments, the formula is (CN+PU)/(CC+PIC), where CC is a Hounsfield unit (HU) value of the corpus callosum mask, CN is a HU value of the caudate nucleus mask, PU is a HU value of the putamen mask, PIC is a HU value of the posterior limb of the internal capsule.

BRIEF DESCRIPTION OF DRAWINGS

Aspects of the present invention are best understood from the following detailed description when read with the accompanying figures. It is noted that, in accordance with the standard practice in the industry, various features are not drawn to scale. In fact, the dimensions of the various features may be increased or reduced for clarity of discussion.

DETAILED DESCRIPTION OF THE INVENTION

It will be appreciated that, although specific embodiments of the present invention are described herein for purposes of illustration, various modifications may be made without departing from the spirit and scope of the present invention.

In the following description, certain specific details are set forth in order to provide a thorough understanding of various aspects of the disclosed subject matter. However, the disclosed subject matter may be practiced without these specific details. In some instances, well-known structures and methods of power delivery comprising embodiments of the subject matter disclosed herein have not been described in detail to avoid obscuring the descriptions of other aspects of the present invention.

Unless the context requires otherwise, throughout the specification and claims that follow, the word "comprise," "have," "include," and variations thereof, such as "comprises," "comprising," "having," "including" are to be construed in an open, inclusive sense, that is, as "including, but not limited to."

Reference throughout the specification to "one embodiment" or "an embodiment" means that a particular feature, structure, or characteristic described in connection with the embodiment is included in at least one embodiment. Thus, the appearance of the phrases "in one embodiment" or "in an embodiment" in various places throughout the specification are not necessarily all referring to the same aspect. Furthermore, the particular features, structures, or characteristics may be combined in any suitable manner in one or more aspects of the present invention.

Figure 2:
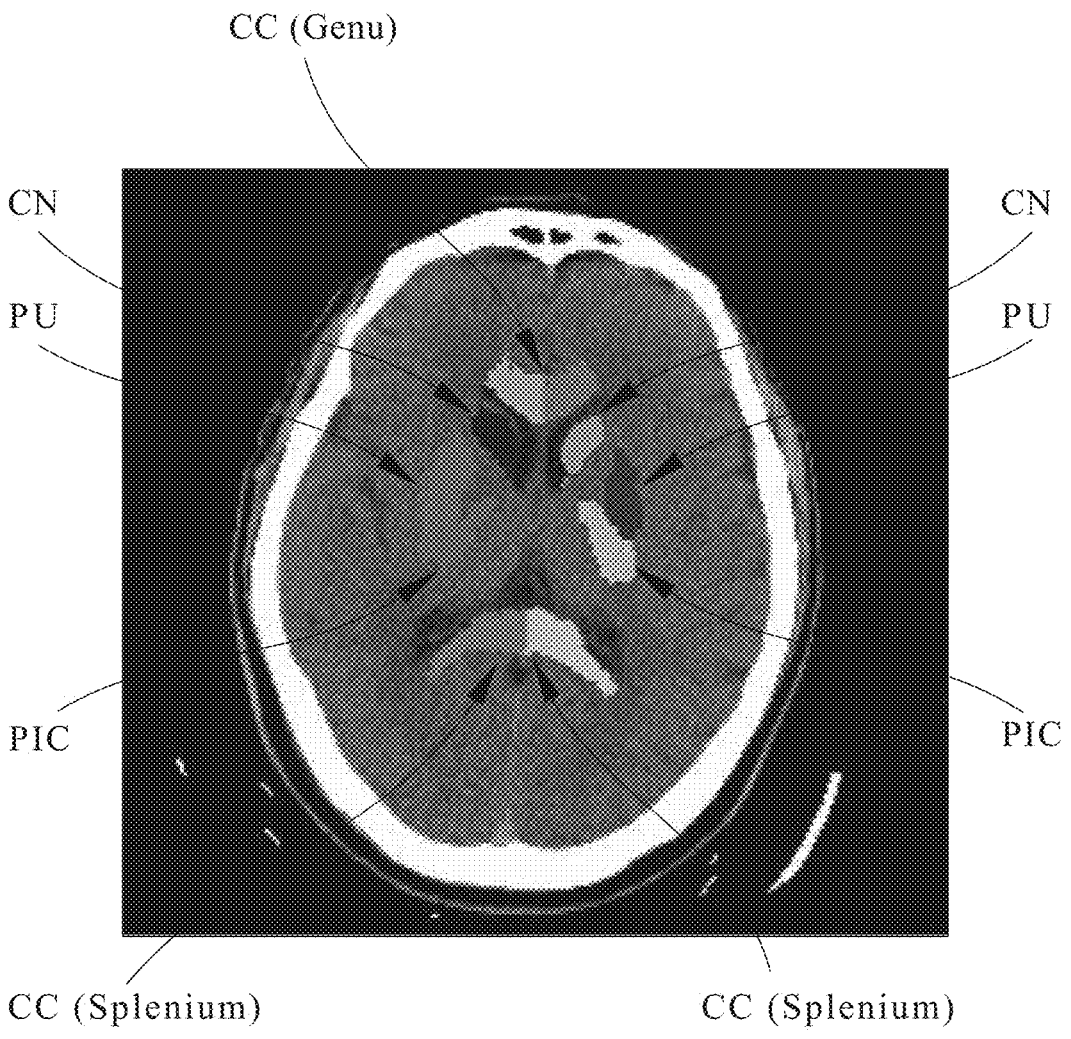
FIG. 2 is a schematic diagram of a computer tomography method used in the automatic calculation method of gray-to-white-matter ratio for head computed tomography of patients with cardiac arrest in accordance with embodiments of the present invention.
Figure 3:
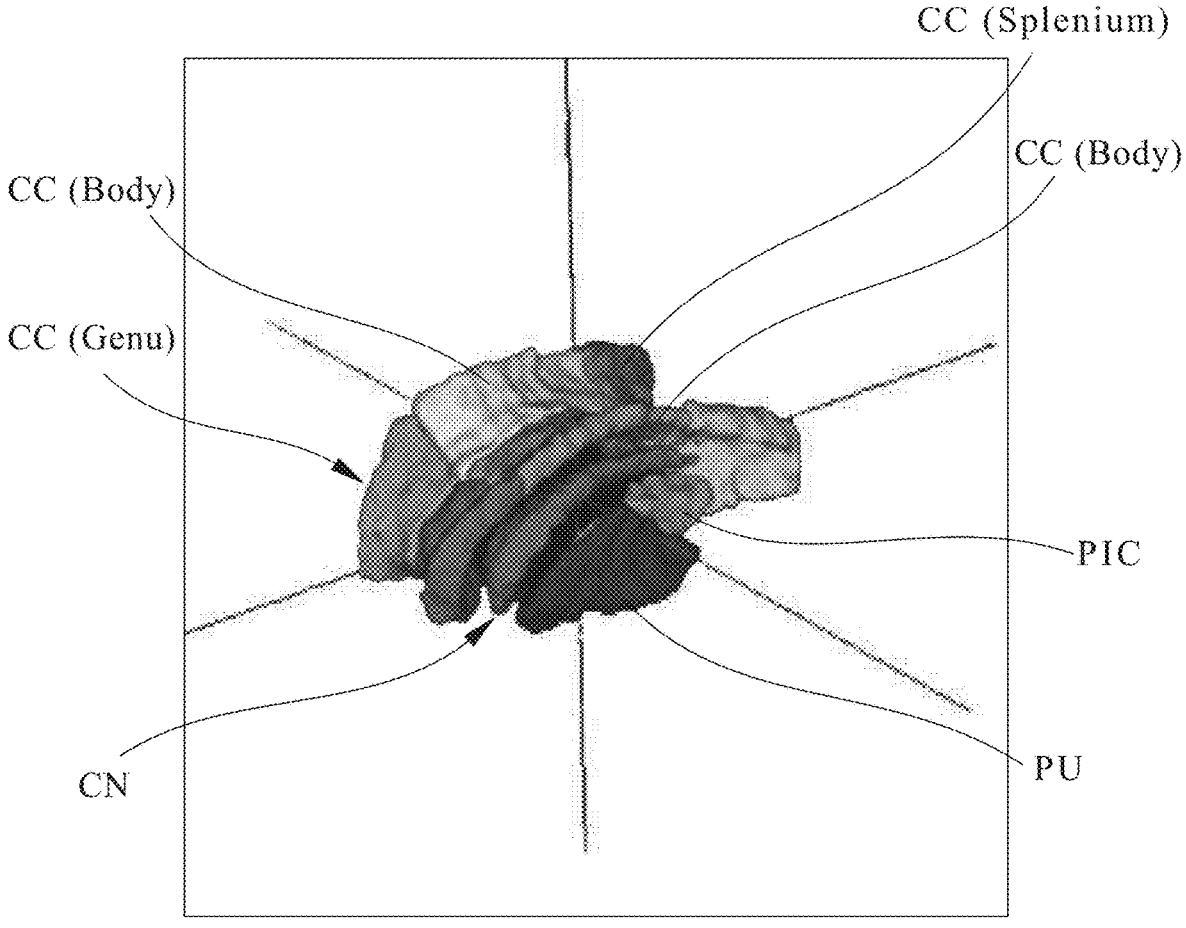
FIG. 3 is a computer 3D schematic diagram of the automatic calculation method of gray-to-white-matter ratio for head computed tomography of patients with cardiac arrest in accordance with embodiments of the present invention.

FIG. 2 is a schematic diagram of a computer tomography method used in the automatic calculation method of gray-to-white-matter ratio for head computed tomography of patients with cardiac arrest in accordance with embodiments of the present invention. FIG. 3 is a computer 3D schematic diagram of the automatic calculation method of gray-to-white-matter ratio for head computed tomography of patients with cardiac arrest in accordance with embodiments of the present invention.

Figure 1:
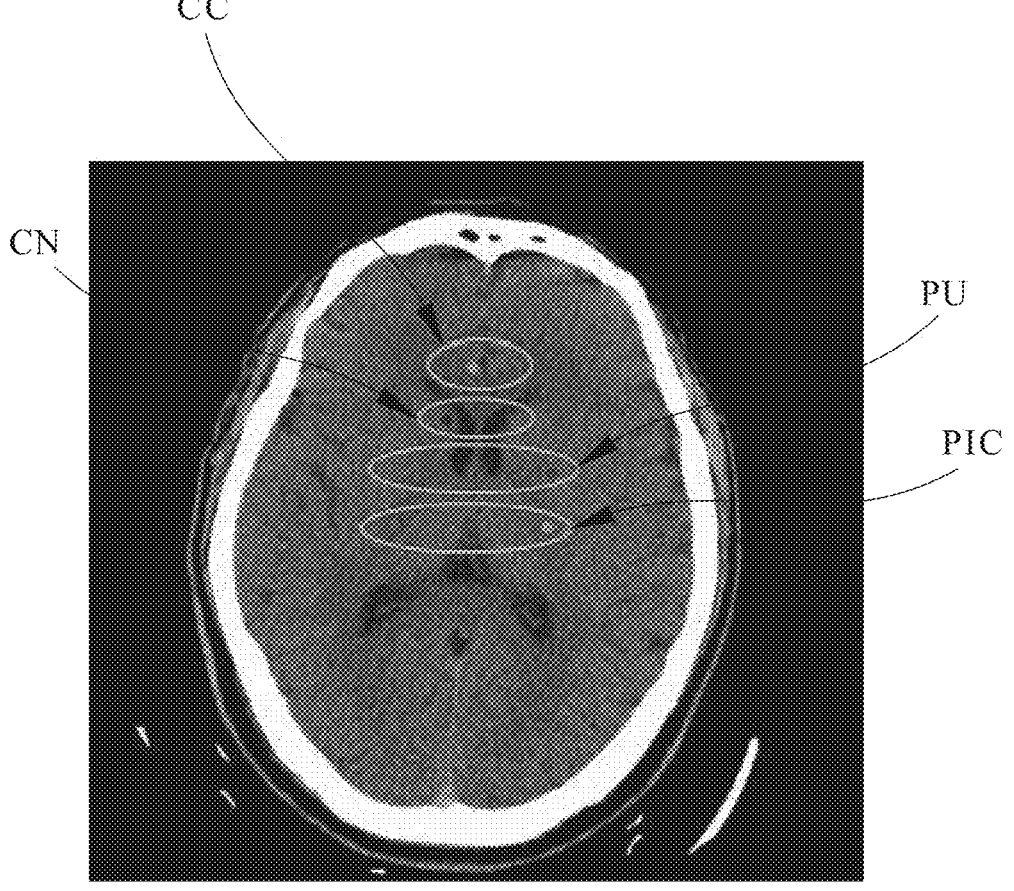
FIG. 1 is a schematic diagram of a conventional computer tomography method for manually calculating the ratio of gray to white matter in computed tomography of the head of a patient with cardiac arrest.

Please refer to FIGS. 2 and 3, the automatic calculation method S100 of the gray-white matter ratio for head computed tomography of patients with cardiac arrest according to the present invention (refer to FIG. 4 described below) is for the computer to automatically find the corpus callosum CC, caudate nucleus CN, putamen PU, posterior branch of the internal cerebral cyst PIC and other regions of the left and right brain through the following processing steps (i.e. refer to S110~S140 in FIG. 4 described below), as shown in FIG. 2. It should be noted that the automatic calculation method S100 of the gray-white matter ratio for head computed tomography of patients with cardiac arrest according to the present invention circles the 3D structure of the corpus callosum CC, the caudate nucleus CN, the putamen PU, and the posterior branch of the internal brain capsule PIC of the left and right brains, instead of the manually circled plane circle area of prior art (as shown in FIG. 1).

Figure 4:
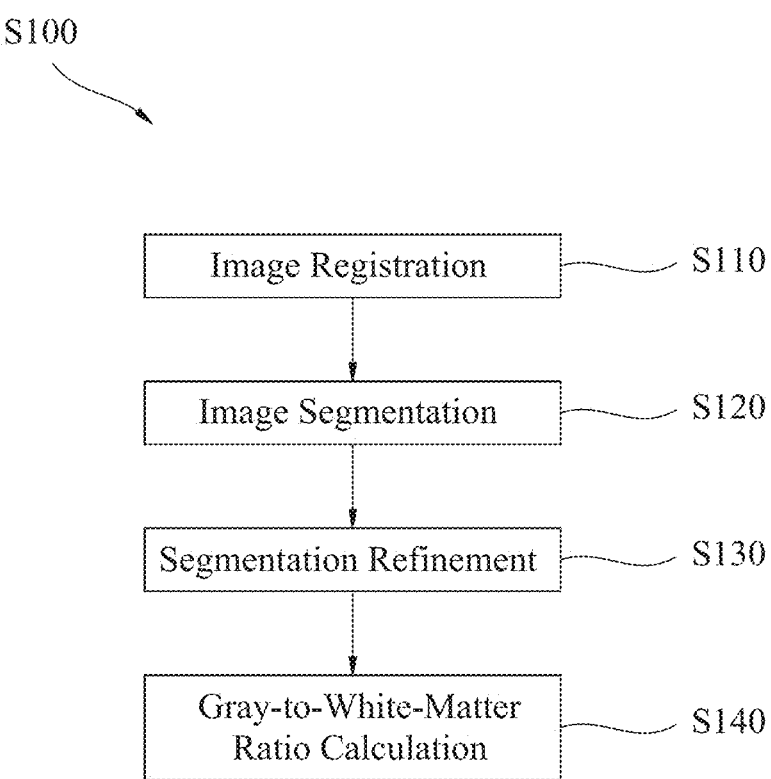
FIG. 4 is a flowchart of the automatic calculation method of gray-to-white-matter ratio for head computed tomography of patients with cardiac arrest in accordance with embodiments of the present invention.

FIG. 4 is a flowchart of the automatic calculation method of gray-to-white-matter ratio for head computed tomography of patients with cardiac arrest in accordance with embodiments of the present invention.

Please refer to FIG. 4, the automatic calculation method S100 of the gray-white matter ratio for head computed tomography of patients with cardiac arrest according to the present invention includes an image registration step S110, an image segmentation step S120, a segmentation refinement step S130, and a gray-and-white-matter ratio calculation step S140.

Figure 5:
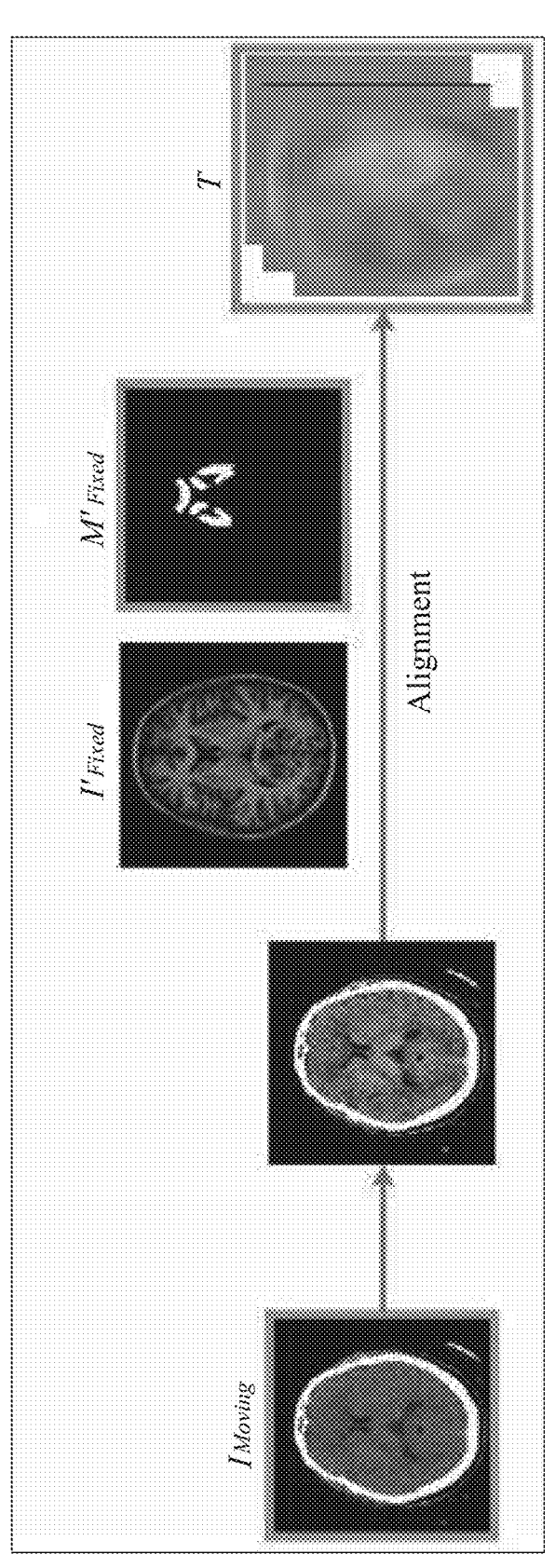
FIG. 5 is a schematic diagram of the image registration step of the automatic calculation method of gray-to-white-matter ratio for head computed tomography of patients with cardiac arrest in accordance with embodiments of the present invention.

FIG. 5 is a schematic diagram of the image registration step of the automatic calculation method of gray-to-white-matter ratio for head computed tomography of patients with cardiac arrest in accordance with embodiments of the present invention.

Please refer to FIG. 4 and FIG. 5 at the same time, in the image registration step S110, performing a pre-process on a patient's head computed tomography image $I_{Moving}$ to enhance the image contrast firstly, and then aligning with a standard brain magnetic resonance imaging (MRI) image $I'_{Fixed}$. The purpose of the alignment is to allow a known standard brain annotation $M'_{Fixed}$ to be applied to the patient's head computed tomography image $I_{Moving}$. In some embodiments, the pre-processing may be contrast limited adaptive histogram equalization (CLAHE), and the contrast limited adaptive histogram equalization is to make the alignment more accurate.

Figure 6:
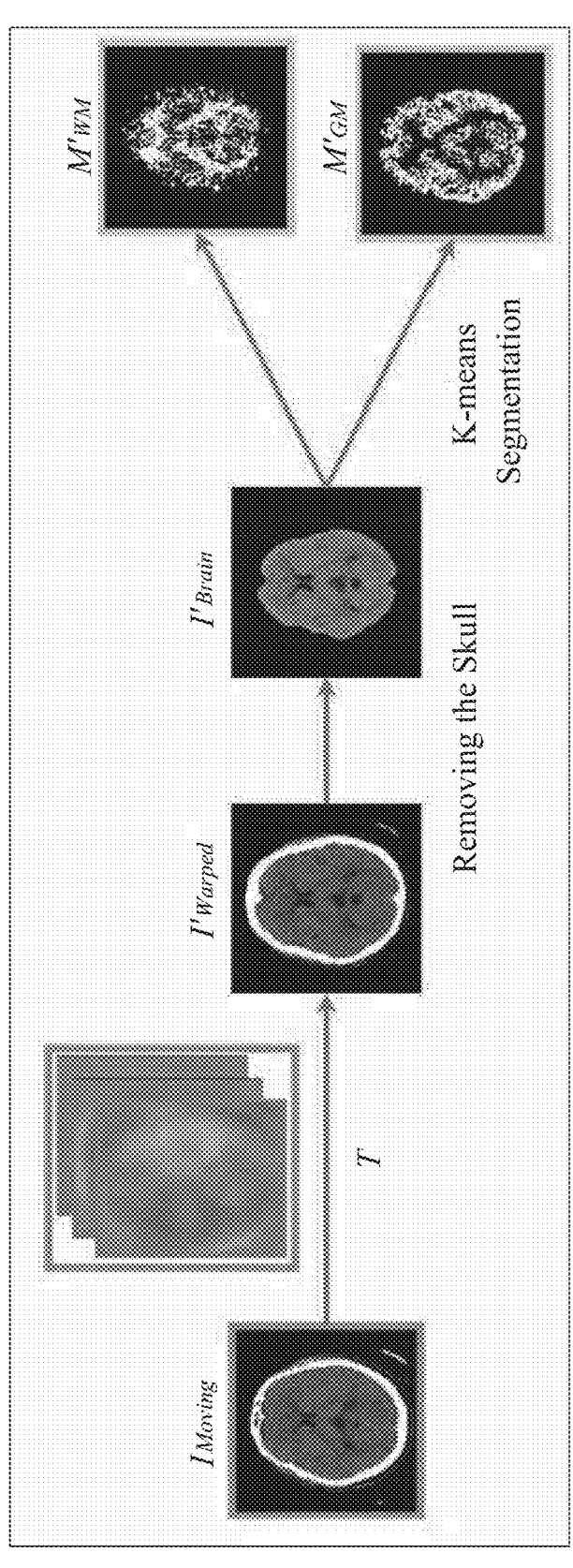
FIG. 6 is a schematic diagram of the K-means segmentation step of the automatic calculation method of gray-to-white-matter ratio for head computed tomography of patients with cardiac arrest in accordance with embodiments of the present invention.

FIG. 6 is a schematic diagram of the K-means segmentation step of the automatic calculation method of gray-to-white-matter ratio for head computed tomography of patients with cardiac arrest in accordance with embodiments of the present invention.

Please refer to FIG. 4 and FIG. 6 at the same time, in the image segmentation step S120, applying a transformation T of the alignment to the patient's head computed tomography image $I_{Moving}$ to obtain an aligned patient computed tomography image $I'_{Warped}$; removing the skull to obtain a brain image $I'_{Brain}$; then using K-Means segmentation to obtain a gray matter mask $M'_{GM}$ and a white matter mask $M'_{WM}$ of the whole brain. In some embodiments, the transformation T is a vector field that combines an affine transformation and a nonlinear transformation. The purpose of K-Means is to subsequently improve the known standard brain annotation $M'_{Fixed}$ error on the patient's computed tomography image $I'_{Warped}$ after alignment caused by alignment error.

Figure 7:
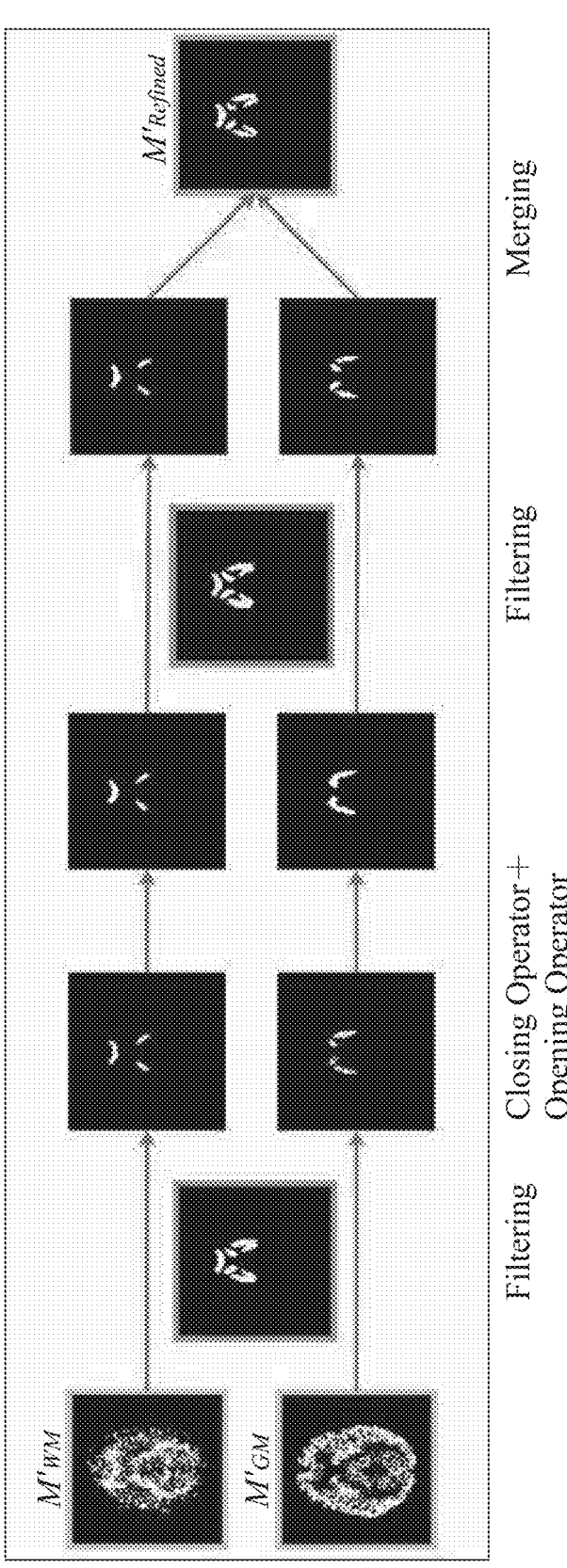
FIG. 7 is a schematic diagram of the segmentation refinement step of the automatic calculation method of gray-to-white-matter ratio for head computed tomography of patients with cardiac arrest in accordance with embodiments of the present invention.

FIG. 7 is a schematic diagram of the segmentation refinement step of the automatic calculation method of gray-to-white-matter ratio for head computed tomography of patients with cardiac arrest in accordance with embodiments of the present invention.

Please refer to FIG. 4 and FIG. 7 at the same time, in the segmentation refinement step S130, filtering the gray matter mask $M'_{GM}$ and white matter mask $M'_{WM}$ respectively using the parts of gray matter and white matter in the known standard brain annotations $M'_{Fixed}$; using a closing operator and an opening operator in a morphology to perform a noise removal process, such as filling small holes and removing speckle noise; then filtering again using the known standard brain annotation $M'_{Fixed}$; finally, merging the gray matter mask $M'_{GM}$ and the white matter mask $M'_{WM}$ to obtain a refined standard brain annotation $M'_{Refined}$. Since the gray matter mask $M'_{GM}$ and the white matter mask $M'_{WM}$ are fragmented, but the desired anatomical position is a continuous volume, common computer vision methods can be used to fill small holes and removing speckle noise.

Figure 8:
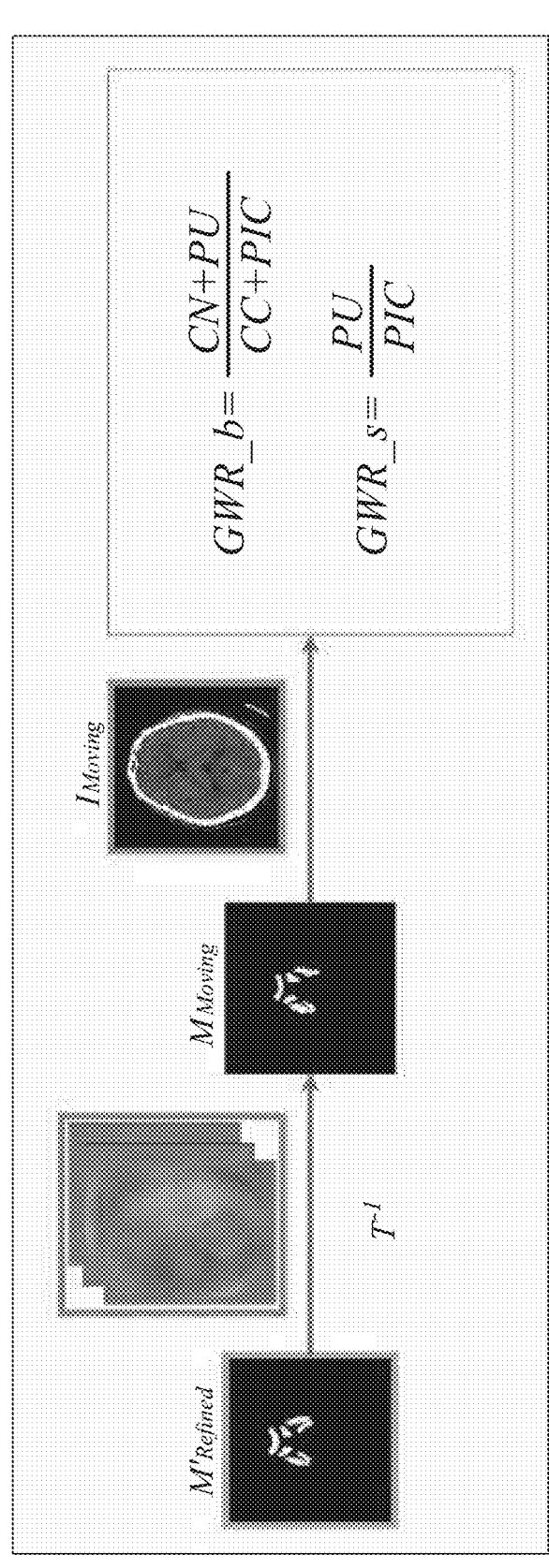
FIG. 8 is a schematic diagram of the gray-to-white-matter ratio calculation step of the automatic calculation method of gray-to-white-matter ratio for head computed tomography of patients with cardiac arrest in accordance with embodiments of the present invention.

FIG. 8 is a schematic diagram of the gray-to-white-matter ratio calculation step of the automatic calculation method of gray-to-white-matter ratio for head computed tomography of patients with cardiac arrest in accordance with embodiments of the present invention.

Please refer to FIG. 4 and FIG. 8 at the same time, in the gray-to-white-matter ratio calculation step S140, converting the refined standard brain annotation $M'_{Refined}$ from a standard brain domain back to the patient CT domain using an inverse transformation $T^{-1}$ to an improved brain mask $M_{Moving}$; finally, applying a formula to the original patient's head computed tomography image $I_{Moving}$ to calculate a gray-to-white matter ratio GWR_b. In some embodiments, it may be the inverse transformation $T^{-1}$ of the aforementioned transformation T. In some embodiments, the brain mask $M_{Moving}$ may include a corpus callosum mask, a caudate nucleus mask, a putamen mask, and a posterior branch of the internal brain capsule mask of the left and right brains.

In some embodiments, the formula in the gray-to-white-matter ratio calculation step S140 is GWR_b=(CN+PU)/(CC+PIC), where CC is a Hounsfield unit (HU) value of the corpus callosum mask, CN is a HU value of the caudate nucleus mask, PU is a HU value of the putamen mask, PIC is a HU value of the posterior limb of the internal capsule. In some other embodiments, the gray-to-white matter ratio calculation step S140 may be to calculate a simplified gray-to-white-matter ratio GWR_s, the simplified formula of which is GWR_s=PU/PIC.

Therefore, through the above method, measure the gray-white-matter ratio through brain computed tomography early after cardiac arrest to automatically locate the areas of corpus callosum, caudate nucleus, putamen, and posterior limb of the internal capsule. It is a 3D three-dimensional structure rather than a manually circled flat circular area to evaluate the effectiveness of predicting neurological prognosis at discharge.

The invention claimed is:

1. An automatic calculation method of gray-to-white-matter ratio for head computed tomography of patients with cardiac arrest, comprising:

an image registration step: performing an alignment on a patient's head computed tomography image and a standard brain magnetic resonance imaging (MRI) image;

an image segmentation step: applying the patient's head computed tomography image to a transformation of the alignment to obtain an aligned patient's computed tomography image, then removing a skull to obtain a brain image, and then using a K-Means segmentation to obtain a gray matter mask and a white matter mask of a whole brain;

a segmentation refinement step: filtering the gray matter mask and the white matter mask separately, using a morphology to perform a noise removal process, then filtering again, and merging the gray matter mask and the white matter mask to obtain a refined standard brain annotation; and a gray-to-white-matter ratio calculation step: converting the refined standard brain annotation from a standard brain domain back to a patient computed tomography domain by an inverse transformation to obtain a brain mask, and finally, applying a formula based on the patient's head computed tomography image to calculate a gray-to-white matter ratio, wherein in the gray-to-white-matter ratio calculation step, the brain mask includes a corpus callosum mask, a caudate nucleus mask, a putamen mask, and a posterior limb of the internal capsule mask for the left and right brain regions.

2. The method according to claim 1, wherein the image registration step further comprises performing a pre-process on the patient's head computed tomography image.

3. The method according to claim 2, wherein the pre-process is contrast limited adaptive histogram equalization.

4. The method according to claim 3, wherein the alignment is applied a known standard brain annotation to the patient's head computed tomography image.

5. The method according to claim 1, wherein the transformation in the image segmentation step is a vector field that combines affine transformation and nonlinear transformation, and the inverse transformation is the inverse transformation of this vector field.

6. The method according to claim 4, wherein in the segmentation refinement step, using the parts of gray matter and white matter in the known standard brain annotation to filter the gray matter mask and the white matter mask, and using the known standard brain annotation to perform the step of filtering again.

7. The method according to claim 6, wherein in the segmentation refinement step, using a close operator and an open operator in the morphology to perform the noise removal process.

8. The method according to claim 7, wherein the noise removal process includes filling small holes and removing speckle noise.

9. The method according to claim 1, wherein the formula is (CN+PU)/(CC+PIC), where CC is a Hounsfield unit (HU) value of the corpus callosum mask, CN is a HU value of the caudate nucleus mask, PU is a HU value of the putamen mask, PIC is a HU value of the posterior limb of the internal capsule.

* * * * *